United States Patent
Sedgwick et al.

(10) Patent No.: US 6,298,263 B1
(45) Date of Patent: Oct. 2, 2001

(54) ODOR EVALUATION

(75) Inventors: Edward Michael Sedgwick, Eastleigh; Mehri Sarfarazi, Southampton; Anne Richardson; John Martin Behan, both of Ashford; Steve Van Toller, Kenilworth; Joanne Allison Grigor, Gainsborough, all of (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/402,354

(22) PCT Filed: Apr. 3, 1998

(86) PCT No.: PCT/GB98/00989

§ 371 Date: Feb. 14, 2000

§ 102(e) Date: Feb. 14, 2000

(87) PCT Pub. No.: WO98/44843

PCT Pub. Date: Oct. 15, 1998

(30) Foreign Application Priority Data

Apr. 4, 1997 (EP) .................................. 97302324

(51) Int. Cl.[7] ........................................... A61B 5/04

(52) U.S. Cl. ............................................. 600/544

(58) Field of Search ..................... 600/544, 545

(56) References Cited

PUBLICATIONS

Lorig: "Chemosensory Modulation of Visual and Auditory Event–Related Potentials" Proceeding of the Annual International Conference of the IEEE Engineering in Medicine and Biology Society, Oct. 31–Nov. 3, 1991, vol. 13, No. PART 02/05, Oct. 31, 1991, Nagel et al p. 548/549 XP000348346 see p. 548, left hand col, line 1, p. 549, left hand col, line 29, tables 1,2.

Mathe et al: "Clinical Application of Evoked Potentials and CNV for Objective Olfactometry" Proceedings of the Annual International Conference of the IEEE Engineering in Medicine and Biology Society, Oct. 31 –Nov. 3, 1991, vol. 13, No. PART 02/05, Oct. 31, 1991, Nagel et al p. 543 XP000348343 see p. 453 left hand col, line 1 right hand col, line 14, table 1.

*Primary Examiner*—John P. Lacyk
*Assistant Examiner*—N Natniththadha
(74) *Attorney, Agent, or Firm*—Pillsbury Winthrop LLP

(57) ABSTRACT

A method of odor selection for selecting an odor to match a visual or auditory target stimulus, comprising evaluating a number of odor/target stimulus combinations by testing a subject by presenting the subject with one or more odors under different conditions, at least some conditions being in the presence of one or more target stimuli monitoring brain activity of the subject and evaluating the monitored brain activity in relation to odor/target stimulus combinations presented to the subject and selecting the odor/target stimulus combination or combinations indicated as having the greatest degree of association.

12 Claims, 13 Drawing Sheets

Fig. 13.

| | FREQUENT | RARE |
|---|---|---|
| FT8 | -4.27 | -6.47 |
| T4 | -0.77 | -5.66 |

| | FREQUENT | RARE |
|---|---|---|
| FC4 | -0.20 | -4.91 |
| C4 | 0.63 | -4.76 |
| CP4 | 1.76 | -3.71 |
| P4 | 2.65 | -1.59 |
| TP8 | 2.69 | -2.35 |

| | FREQUENT | RARE |
|---|---|---|
| FZ | 0.32 | -3.78 |
| CZ | -0.17 | -6.49 |
| CPZ | 0.51 | -4.78 |
| PZ | 1.27 | -3.47 |

| | FREQUENT | RARE |
|---|---|---|
| FC3 | 0.20 | -5.12 |
| C3 | -0.52 | -4.69 |
| CP3 | -0.17 | -4.57 |
| P3 | 0.89 | -3.06 |
| TP7 | -0.30 | -3.58 |

| | FREQUENT | RARE |
|---|---|---|
| FT7 | -4.25 | -6.03 |
| T3 | -1.49 | -3.66 |

ODOR EVALUATION

This application is the national phase of international application PCT /GB98/00989 filed Apr. 3, 1998 which designated the U.S.

FIELD OF THE INVENTION

This invention relates to odour evaluation and odour selection.

BACKGROUND OF THE INVENTION

In designing a new fragrance many considerations have to be taken into account. First and foremost is the need to have an aesthetically acceptable and safe blend of odorous ingredients which perform adequately in the product form which will be used by consumers. However, it is increasingly important that a fragrance is also designed as far as possible to support the intended market positioning and emotional values of a product. For example, the odour may be required to be compatible with and appropriate for a "caring/ reassuring" positioning or to connote "fresh, clean, invigorating". Achieving these objectives lies within the skill and experience of skilled perfumers and perfumery experts, supported by consumer research and related fields. Nevertheless, despite the combined best efforts of all involved it is still remarkably difficult to design and select successful fragrances, particularly in new odour areas.

It is particularly difficult to gain an understanding of how consumers will perceive a fragrance in terms of positioning in advance of launching a product. Some associations can be probed by consumer research techniques such as surveys and focus groups. These improve our understanding of product attributes and consumer attributes, preferences and sensitivity. However, it is likely there will be also implicit, non-conscious associations which the consumer will not be able or willing to verbalise spontaneously and which could elude even the most probing questioning. The objective of this invention is to probe these implicit associations as a basis to aid odour selection and fragrance design.

SUMMARY OF THE INVENTION

In one aspect the present invention provides a method of odour evaluation for evaluating an odour in relation to a target, comprising testing a subject by presenting the subject with one or more odours under different conditions, at least some being in the presence of one or more targets; monitoring brain activity of the subject; and evaluating the monitored brain activity in relation to odour/target combinations presented to the subject.

Experiments by the present inventors have shown that if a subject is presented with a related odour and target (eg a rose odour and a visual image of a rose) at the same time, the brain activity of the subject is different from that in other circumstances, namely when presented with a less related odour and target (eg a rose odour and a visual image of a flower that is not a rose), an unrelated odour and target (eg a rose odour and an unrelated, non-floral visual image), a target but no odour, or an odour but no target. Brain activity can thus provide an objective measure of the relatedness (or congruence) of an odour and target.

Evaluation of brain activity for odour/target combinations presented to a subject can thus provide a measure of the degree of association between the odour and target in a particular odour/target combinations. These measures can be compared and used as a basis of odour selection, as will be described below.

It is preferred to monitor electrical activity of the brain, preferably event-related potentials (ERPs) which are conveniently monitored using electroencephalography (EEG). Electrical activity on the subject's scape midline at least is preferably monitored.

EEG provides a gross measure of the electrical activity of the brain recorded from the surface of the scalp. In monopolar recording, one electrode is placed above a particular brain structure and the other to a reference point, for example an earlobe. In biopolar recording, the EEG signal is recorded between electrodes placed at two active sites.

The scalp activity reflects the sum of electrical events throughout the head. These include brain activity but also electrical signals from skin, muscles, blood and eyes. Thus if the EEG is to be free of 'artefacts' the subject is required to be still and sensorily isolated. Clinically EEG is useful as a diagnostic tool enabling some recognisable EEG wave forms to be identified which are associated with particular states of consciousness or particular types of cerebral pathology.

Spontaneous EEG has been used to show correlations between psychometric properties of odour and spontaneous brain activity in real time following olfactive events.

Event-related potentials are characteristic wave forms associated with a particular stimulus or event. For example, the sensory evoked potential is the change in the cortical EEG signal elicited by the momentary presentation of a sensory stimulus. The stimulus is presented for a very short period of time, typically 10 msecs, and events are recorded for up to 2 seconds after stimulus presentation. The background EEG is often too noisy to see ERPs, thus the experiment needs to be repeated a large number of times and identical scans averaged to yield a high signal:noise ratio. For odour this could typically be 40–100 scans.

Each peak or wave of the elicited ERPs is characterised by whether it is positive or negative and by its latency. For example, the P300 wave is the positive wave that usually occurs about 300 msec after a momentary stimulus only if it has considerable meaning for the subject. In contrast, the small waves recorded in the first few milliseconds after a stimulus are not easily influenced by changing the meaning of the stimulus. They represent primary sensory processing in the brain. Later signals, from say 100 msec, change their characteristics according to the meaning or context of the stimulus. These later potentials are referred to as "event-related potentials" or "cognitive evoked potentials".

Good results have been obtained by studying variations in the N400 potential, ie the negative peak occurring between about 350 and 600 msec after presentation of the target stimulus. It has been found that the N400 deflection is significantly greater if there is no match or congruence between a simultaneously presented odour and target, enabling identification of related or congruent odour/target combinations. Readings from electrodes on the scalp midline, eg at the frontal midline position (Fz) and the parietal midline position (Pz), have been found particularly useful.

EEG is a particularly useful method for monitoring brain response. EEG can be used both qualitatively and quantitatively; there are a variety of reliable instruments commercially available to record EEG; the measurements can be obtained from electrodes attached to the surface of a subject's scalp with a minimum of discomfort; the number and location of electrodes and can be adjusted to focus on specific structures; the timecourse of activity can be monitored either in real time (for spontaneous activity with or without a stimulus) or following presentation of a stimulus; and finally the frequency of the brain activity can be measured (eg the "alpha" frequency waveband lies between 8 and 13 Hz).

It is known that brain waves change during the perception of odours. This has been related to familiarity, intensity and pleasantness in the frontal region for spontaneous EEG. Although no systematic patterns were identified, it was hypothesised that activity measured in a frontal region was related to evaluation of odour.

Odour can affect mood and this topic has been discussed (J S Jellinek (1994)), Aromachology: A status review. Perfumer and Flavourist, 19, 25–49) under the title of Aromachology. Aromatherapy involves changing physical and psychological states by massage and essential oils topically applied neat or in a neutral carrier.

Work has been carried out investigating changes in visual evoked potentials in the presence of odour. This work primarily investigated odour labelling, and found that presentation of the odour coupled with the requirement to accurately label it evokes a slow negativity which peaks at about 280 msec post-label and lasts until about 900 msec. The labelling process requires recall and recognition and as such is an "explicit" process requiring conscious thought.

There is no basis from the literature to expect that vision and odour would lead to similar brain activity in similar psychological tests. For example, for vision and audition, increases in spontaneous alpha wave EEG are believed to be associated with relaxation, whilst there is evidence that the opposite is true for odour (W R Klemm et al (1992), Chemical Senses, 17, No. 3. p.347–361).

There is no literature related to brain activity of congruent and incongruent odour stimuli. There have been studies of congruence between words and pictures. It has been found that evoked potentials for congruent pairs of pictures and words lead to increased negativity in brain activity (eg measurable in the alpha frequency band) particularly between 400 and 600 msec after stimulus presentation.

Psychological tests relating odour and names have also been carried out. Linkages between odour and words have been investigated eg to assess if priming is possible. This work was inconclusive and no strong evidence of priming was found.

Against this background, the demonstration by the present inventors that odours lead to different brain activity when combined with congruent and incongruent stimuli is most surprising and completely unpredictable.

The target will generally be visual or auditory in nature. A visual target may be in the form of one or more photographs, drawings, colours, written words, phrases or logos or other still images, a film or video sequence, or one or more objects, in each case possibly depicting or representing a product (eg soap powder, shampoo etc), a setting (eg a happy domestic scene), an environment (eg a bathroom environment), a relationship (eg a mother and baby), an emotion or mood (eg happiness), an outdoor scene (eg a mountain scene), an activity (eg a cricket match) etc. An auditory target may be in the form of, eg, spoken words, a musical phrase or sequence, a sound effect, a conversation, animal sounds etc.

The odour or odours under test may, for instance, be one or more fragrances, fragrance components or fragranced products such as fabric conditioners, shampoos, cosmetics or bath/shower products containing fragrance. In the case of fragrance components, a final fragrance may be built up from one or more components selected in relation to a particular target with the aid of the invention.

Tests will typically be carried out on a plurality of different subjects, and the results of the tests analysed and combined to give overall test results.

The subject may be required to react to presentation of a target, and measurement made of the response time.

The subject is preferably not required to consider the relationship between odour/target combinations during testing.

The method may be used to select from a range of several odours, eg 5, 20, 30 or more, the odour or odours most appropriate to a particular target. Alternatively, one odour can be tested in relation to a range of several, eg 5, 20, 30 or more, different targets to find the most appropriate odour/target combination or combinations.

The odour evaluations for different odour/target combinations can be compared and used as a basis of odour selection, to enable or assist selection of an odour or odours intended for a particular purpose, eg for use in a fragrance for a particular product. For example, the invention can be used to identify the odour or odours indicated by brain activity testing as having the greatest degree of subconscious association with a particular target such as a product. The selected odour or odours can then be used in any desired way in relation to the target, eg in formulating a fragrance for a target product.

The present invention thus provides a method of odour selection for selecting an odour to match a particular target, comprising evaluating a number of odour/target combinations by the odour evaluation method of the invention, and selecting the odour/target combination or combinations indicated as having the greatest degree of association.

The present invention also provides a product perfumed with a fragrance comprising one or more odours selected by the method of the invention using the product or other desired attribute as a target.

The invention will be further described, by way of illustration, in the following Examples and with reference to the accompanying figures in which:

BRIEF DESCRIPTION OF THE DRAWINGS

FIG. 13 shows grand mean values for the electrodes used in FIG. 12 for the matched (frequent) and mismatched (rare) conditions.

EXAMPLE 1

Figure 1:
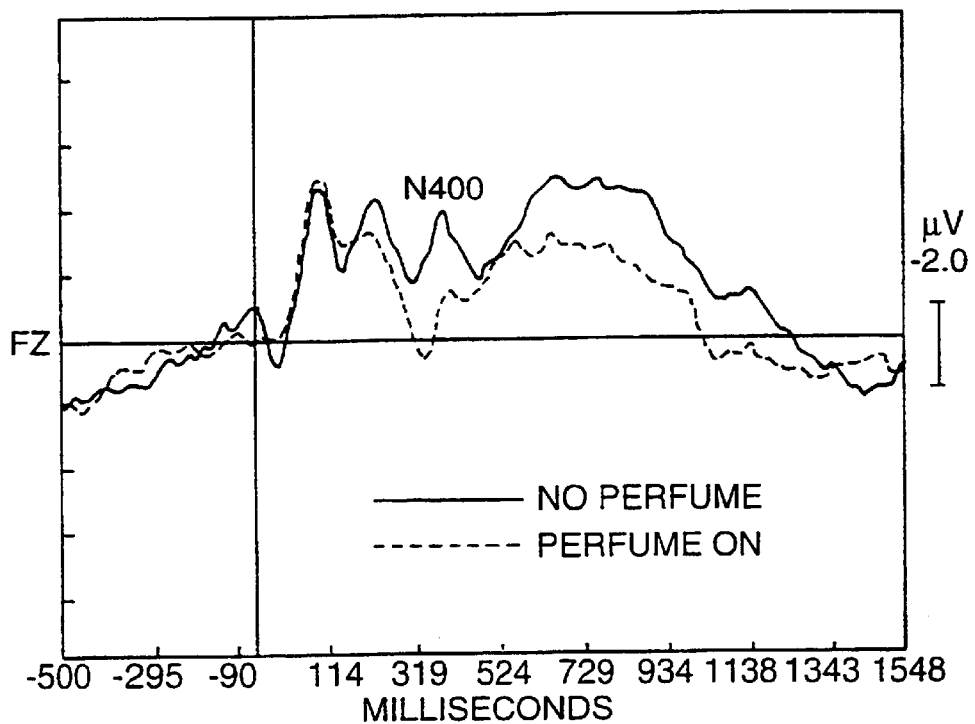
FIGS. 1 and 2 are schematic graphs of potential ($\mu$v) versus time (msec)

In a series of experiments a number of subjects were presented under controlled conditions with a series of visual images of different topics, either in the absence of an odour or in the presence of an odour, the odour being either related or unrelated to the simultaneously presented image. Event-related potential (ERP) traces were recorded via scalp electrodes fitted to the subjects. Analysis and comparison of the results showed there were clear differences between the traces obtained when a subject is presented with a related odour and image at the same time, and the traces obtained in other circumstances.

In detail, the experiments involved testing 20 healthy volunteer subjects.

Each subject was separately tested in a small room, seated on a comfortable reclining chair facing a visual display unit (VDU) for presentation of images. The subject was fitted with a small flexible plastics facial mask, covering the nose and mouth, for delivery of filtered air which has possibly been passed over perfumes under investigation.

16 tin electrodes mounted in a cap were fixed on the head of the subject for measurement of ERPs. The electrodes overlayed 16 positions or regions as defined by the internationally recognised 10–20 system for electrode placement. Four central (Fz,Cz,Pz,Oz) and 12 lateral (Fp1, Fp2, F3, F4, C3, C4, P3, P4, T3, T4, T5) positions were used where F=frontal, C=central, P=parietal, O=occipital and T=temporal, even numbers denote the right side and odd numbers the left, while z indicates the mid line. Electrooculogram (EOG) was recorded from electrodes situated immediately above the right eyebrow, and on the outer canthus of the left eye (eye movement can induce artefacts into the recordings and the experimenter should be sure that it does not contaminate the recordings of brain activity). Conductive jelly was introduced beneath each electrode to reduce contact impedance to usually less than 5 kilohms. EEG amplifiers with a bandwidth of 0.03–30 Hz passed the signals to an analogue to digital converter (ADC) after suitable amplification.

The subject was given a small box with two buttons (left and right) and instructions were given to press either the right or left button depending on the image presented on the VDU, as explained below.

The visual stimuli in this experiment consisted of pre-recorded high quality pictures from classes of objects chosen to suit the experiment. Examples are fruit, flowers, vegetables, buildings, people, food, outdoor scenes etc. Generally there were 150 pictures in each class and they were presented on the VDU screen in front of the subject in random order. Each picture was presented for 2 seconds. During a 2 second interval between pictures the subject was instructed to fixate on a cross in the centre of the screen. Any number of perfumes, odours or odorous products could be used individually or collectively in association with the pictures.

During some sessions perfume was introduced to the subjects by passing air over the perfume and delivering it via the face mask. The perfume presentation device used had computer controlled valves fitted accurately to time the turning on and off of the odours. In this experiment this was synchronised with the timing of the picture presentation so that the odour presentation was strictly controlled to coincide with chosen visual stimuli, and the event was recorded along with the ERP traces in a personal computer.

During running of a test, ERP signals were recorded from 500 msec before the onset of a stimulus, ie presentation of a new picture on the VDU, and they continued for 1540 msec thereafter. In addition, the subjects were asked to press an appropriate button on the box to classify the type of stimulus; the button pressed and the timing in relation to presentation of the stimulus were recorded. The class of the stimulus was also recorded so that correct and incorrect responses and the promptness of the responses were known.

The signals obtained from the scalp were recorded digitally in a personal computer and later examined for artefacts. Contaminated traces were rejected. Each trace was labelled according to the type of visual stimulus, the odour stimulus if present and whether the subject identified the stimulus correctly or not. The subject's reaction time from picture presentation to pressing of the appropriate button was also recorded. Where the wrong button was pressed, the result was rejected.

Accepted signals were averaged according to their labels by time locking to the moment of stimulus presentation. Further processing was performed such as smoothing, scaling and measurement of amplitudes and latencies of the waveforms and measurement of the response time for pressing the stimulus classification button. Proprietary software was used for recording and analysis.

The aim of having the subject classify the pictures by pressing a button is in part to ensure continued concentration of the subject on the pictures. Pressing a button affects brain activity but experiments have shown there is no significant effect in the time window 200 to 600 msec post-stimulus that is of most importance in the present invention.

The experiment was conducted in three stages and EEG recordings were made throughout all three stages.

Stage 1 (no odour)

No odour is presented in the filtered air, and the subjects were asked to press the "Yes" button on the hand held box if they see a "floral" picture on the VDU screen and press the "No" button on the box if they see a "non-floral" picture on the screen. A total of 50 floral pictures and 50 non-floral pictures were presented in random order. Each picture was presented for 2 seconds with a 2 second gap in between each picture.

Stage 2 (floral odour)

The subjects were instructed that an odour will be presented in the filtered air via the facial mask, and asked again to press the "Yes" button on the control box if they see a floral picture on the screen and the "No" button if they see a "non-floral" picture on the screen.

The floral odour is turned on for 60 seconds (per-on) and then off for 60 seconds (per-off) repeatedly and picture presentation is continuous throughout as in presentation 1. The odour is cycled on and off in this way to prevent acclimatisation.

Stage 3 (fruity odour)

The procedure of stage 2 was repeated, using a fruity odour and equal numbers of fruity and non-fruity pictures presented in random order.

This experiment presents 4 situation types for each odour:

Type 1: Perfume on with related picture
Type 2: Perfume on with non-related picture
Type 3: No odour with related picture
Type 4: No odour with non-related picture The tests were repeated a suitable number of times for each subject and the signals suitably processed to reduce background and noise and produce identifiable traces.

Figure 2:
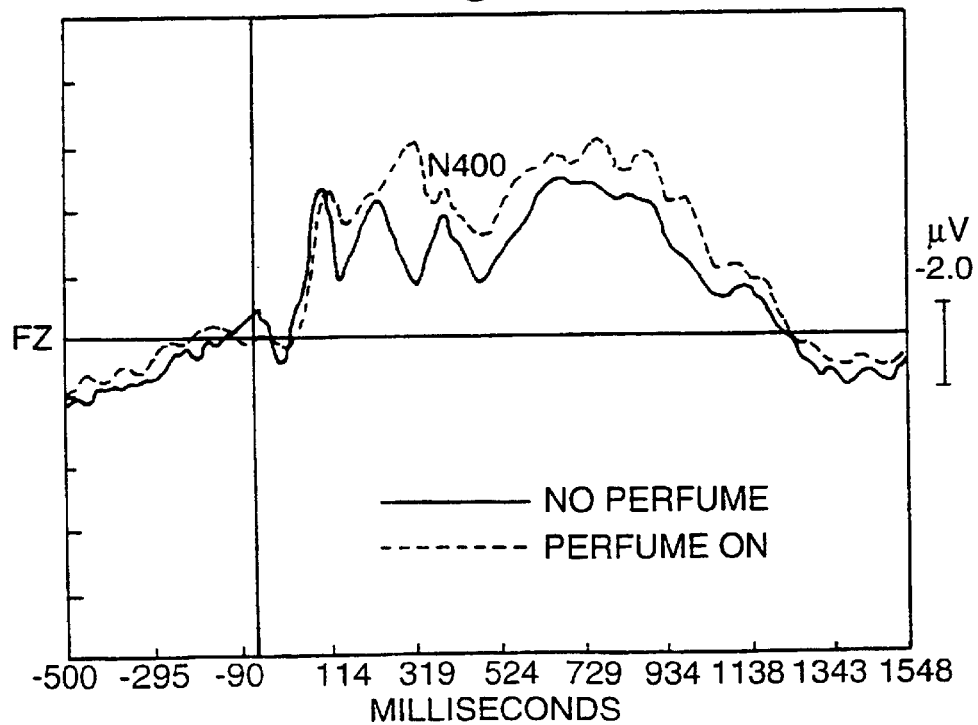

FIG. 1 is a simplified representation of typical ERP traces obtained from a subject viewing a floral picture in the presence of a floral odour (dashed line) and in the absence of odour (full line). FIG. 2 is similarly a simplified representation of typical ERP traces obtained from a subject viewing non-floral pictures in the presence of a floral odour (dashed line) and in the absence of odour (full line). In these Figures and other Figures in the form of graphs of potential versus time, following the usual convention potential is shown increasing from negative at the top of the graphs to positive at the bottom of the graphs.

In FIG. 1 the response after 300 msec is more positive with the odour and related pictures than with the pictures alone. This is thought to reflect the increased ease with which the pictures can be distinguished in the presence of a congruent odour. In FIG. 2 the inappropriate odour is leading to less positively after 300 msec than the no odour (pictures only) control. Perfume is making the association task more difficult.

These simplified graphs demonstrate clearly if a visual stimulus is presented with a related or congruent odour the VEP displays a characteristic pattern, particularly in the time window 200 to 600 msec post stimulus, that can be distinguished from patterns obtained in other circumstances. In particular there is a negative wave (N400) which is greater in amplitude when the two stimuli, picture and odour, do not match (incongruence).

If visual stimuli are combined with a congruent odour the visual evoked potential follow the time course as shown in FIG. 1. It is hypothesised that stimulus aids the more rapid processing, and the latency and negativity reflect the degree of congruency and ease of processing. Where the subject is presented with images incongruent with the odour the time course of evoked potentials is as in FIG. 2. In this case it is hypothesised that more time is required to classify the combination and more detailed processing is required to achieve a classification. This manifests itself as greater N400 and more positively at longer latency.

More detailed results of these experiments are now given.

Behavioural Performance

Accuracy (%) and reaction time (in msec) were measured for each individual and the results are shown in Tables below. Comparison of the accuracy revealed no significant differences. The reaction time was faster when the perfume was on (perfume-on) compared with when the perfume was not presented at all (no-perfume). The paired t test was statistically significant for both floral and fruity perfumes.

TABLE 1

| | Accuracy | | | | | | | |
|---|---|---|---|---|---|---|---|---|
| | Flowers | | Fruits | | Non-related | | Non-related | |
| Flowers | Mean | SD | Mean | SD | Mean | SD | Mean | SD |
| No-perfume | 95.2 | 1.87 | 95.52 | 1.95 | 95.15 | 2.06 | 95.15 | 2.06 |
| Perfume-On | 95.3 | 2.30 | 95.42 | 1.80 | 95.57 | 2.09 | 96.00 | 1.63 |
| Perfume-Off | 95.8 | 1.97 | 95.3 | 1.60 | 96.00 | 2.68 | 95.84 | 2.00 |

TABLE 2

| | Reaction Time | | | | | | | |
|---|---|---|---|---|---|---|---|---|
| | Flowers | | Fruits | | Non-related | | Non-related | |
| Flowers | Mean | SD | Mean | SD | Mean | SD | Mean | SD |
| No-perfume | 688.68 | 14.38 | 798.84 | 114.09 | 765.33 | 133.75 | 765.33 | 133.75 |
| Perfume-On | 657.53 | 129.88 | 720.42 | 160.45 | 697.78 | 161.87 | 691.89 | 128.51 |
| Perfume-Off | 620.42 | 142.22 | 703.68 | 128.95 | 679.33 | 151.60 | 674.84 | 144.86 |

TABLE 3

| | Paired t test-Reaction Time | | | |
|---|---|---|---|---|
| | Floral Flowers | Fruity Fruits | Floral Non-related | Fruity Non-related |
| No-perfume - Perfume On | 0.22 | 0.05* | 0.001* | 0.004* |
| No-perfume - Perfume Off | 0.01* | 0.0006* | 0.001* | 0.001* |
| Perfume-On - Perfume-Off | 0.01* | 0.46 | 0.95 | 0.14 |

*indicates the paired test was statistically significant

ERP Data

As explained above, ERPs were recorded from 16 scalp electrodes from 20 healthy subjects to assess the physiological response to two perfumes (floral and fruity). The ERPs were averaged, beginning 500 msec before to 1540 msec after the stimulus. The results showed the initial evoked responses is the same with or without odour up to 200 msec. Congruent pictures with odour elicited more positive going ERPs, but incongruent pictures with odour elicited more negative going ERPs. The ERPs showed six clear negative (N) and positive (P) peaks, as N120, P180, N280, P340, N400 and P520 (P600) msec. The morphology and latency of these peaks were very similar but not identical in all three conditions with two perfumes.

Figure 3:
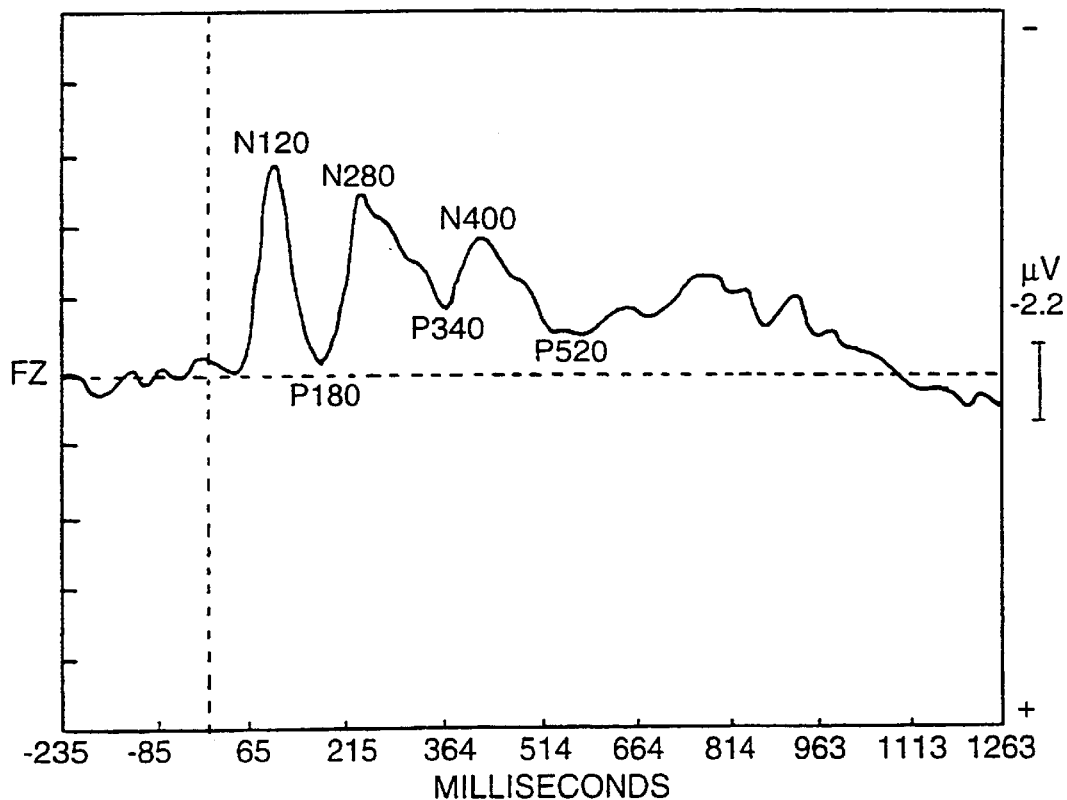
FIG. 3 is a graph of potential ($\mu$v) versus time (msec), showing results from Example 1.

A typical response for the Fz (frontal, midline) electrode is shown in FIG. 3.

A time window was set for 200 to 600 msec post stimulus and all the measurement and statistical analysis have been done in this window of time. The amplitude of the negative peak during this time was measured (N400).

Figure 4A:
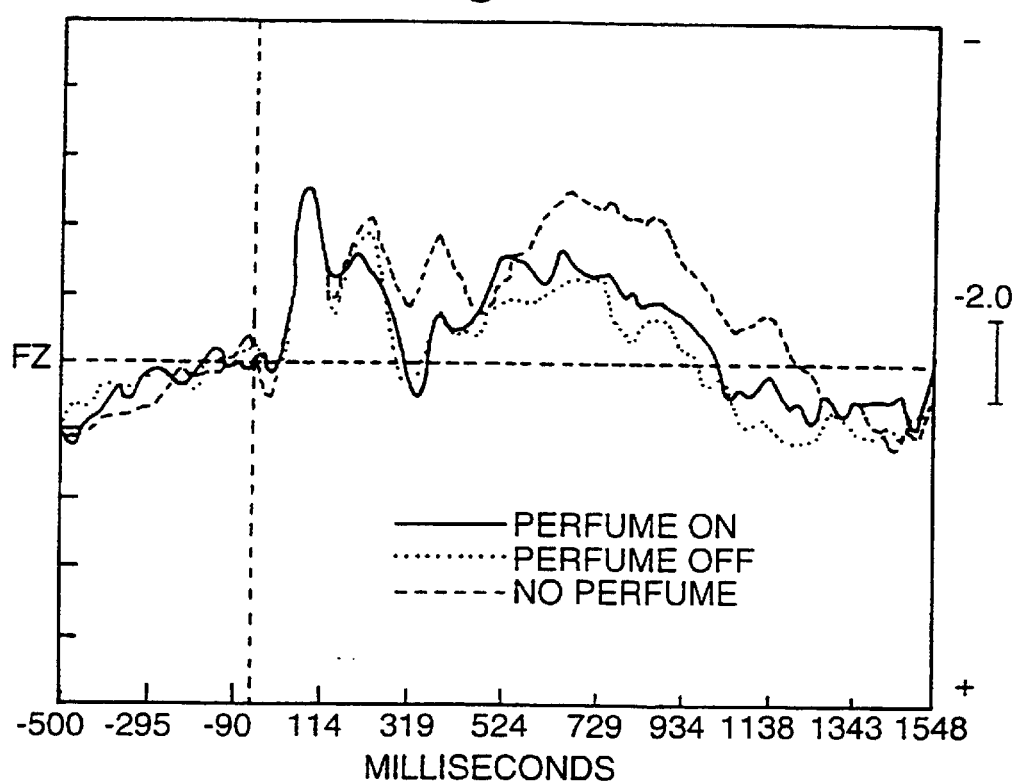
FIGS. 4, 5 and 6 are each pairs of graphs of potential ($\mu$v) versus time (msec), showing results from Example 1.
Figure 4B:
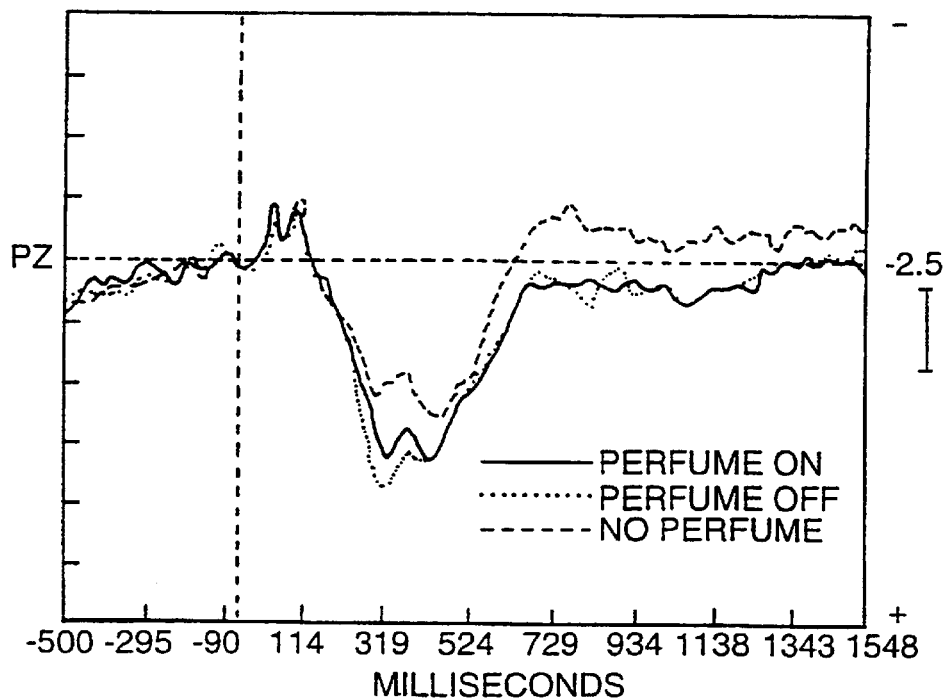

FIG. 4 shows ERP traces for averaged results for the Fz (frontal, midline) electrode (FIG. 4A) and the Pz (parietal, midline) electrode (FIG. 4B) for floral pictures, with the dashed lines showing results for no perfume and the other two lines showing results in the presence of floral perfume, either perfume on for 60 seconds (continuous line) or perfume off for 60 seconds (dotted line). These graphs for grand averages of ERPs evoked with picture of flowers with or without presentation of floral perfume showed that the initial potentials were the same in both conditions up to 200 msec post stimuli. The ERPs to pictures of flowers while the perfume was presented to the subjects elicited more positive-going ERPs, eg N400 was smaller. The N400 component was maximal frontally and P600 component posteriorly.

Figure 5A:
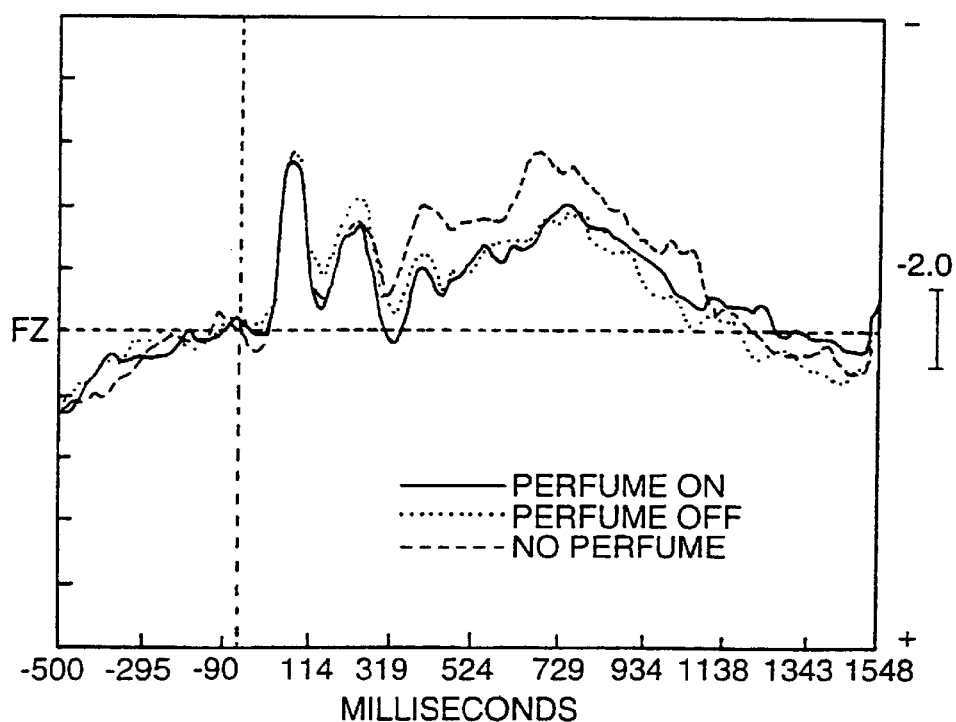
Figure 5B:
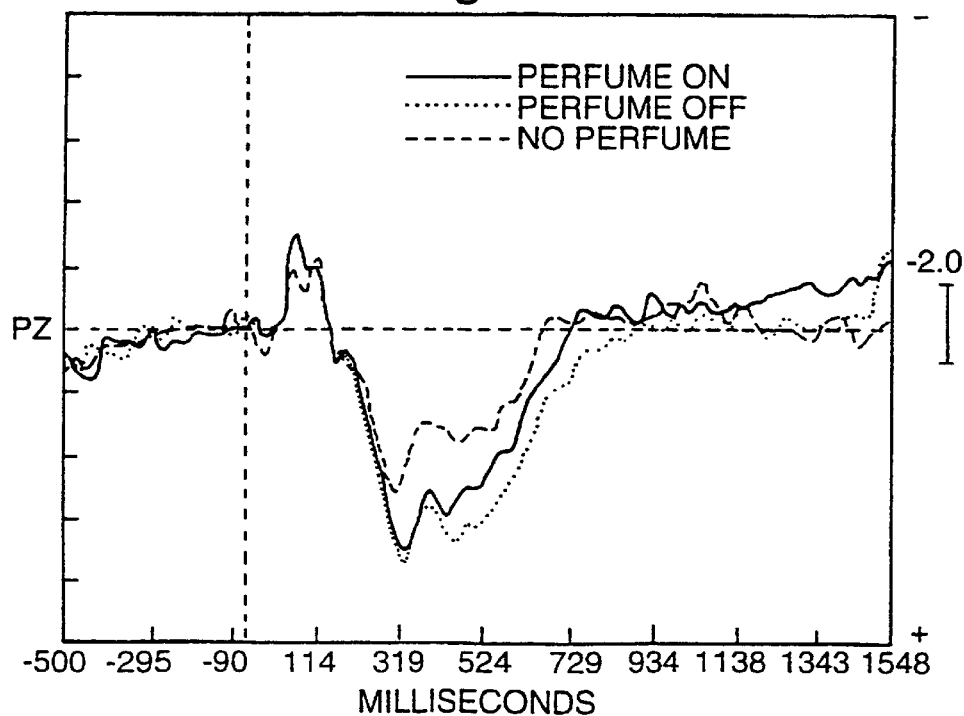
Figure 6A:
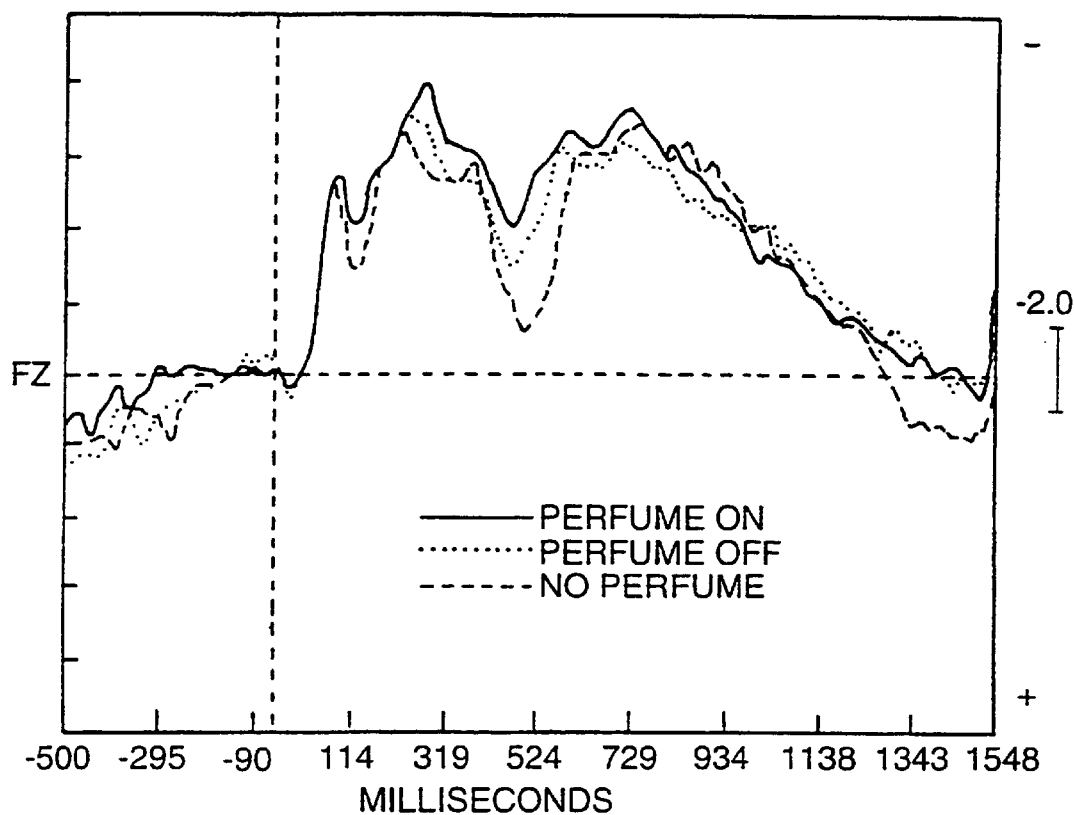
Figure 6B:
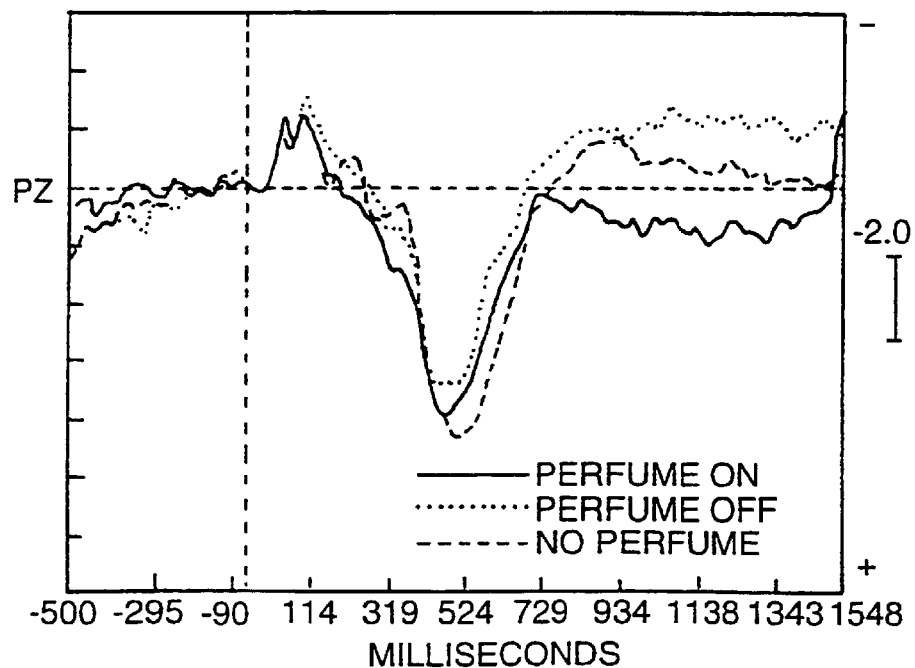
Figure 8A:
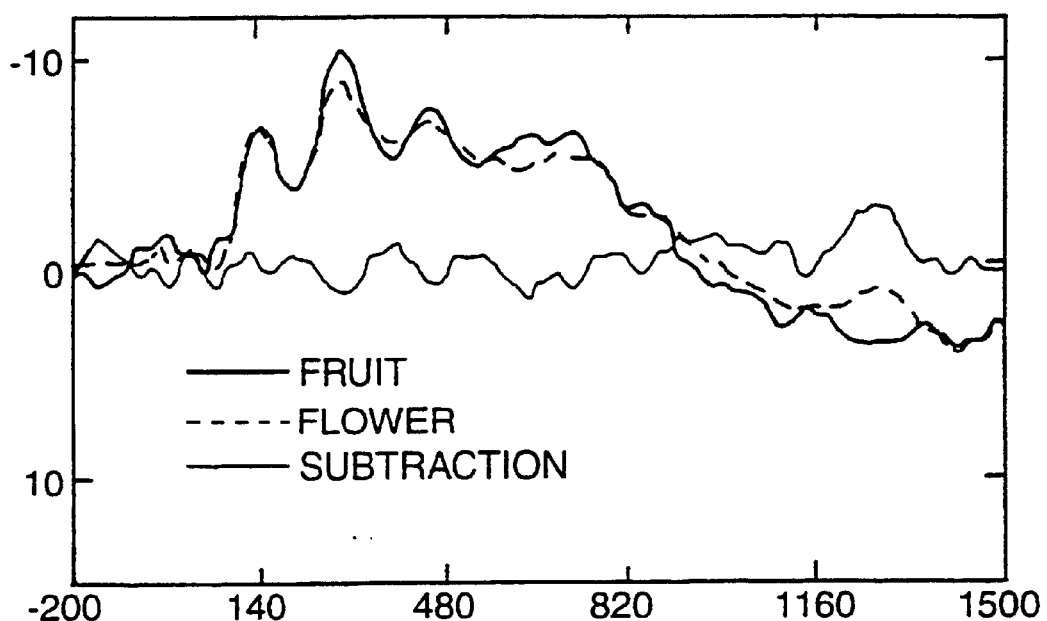
FIG. 8 is a series of graphs of potential ($\mu$v) from Fz electrodes versus time (msec), showing results from Example 3.
Figure 8B:
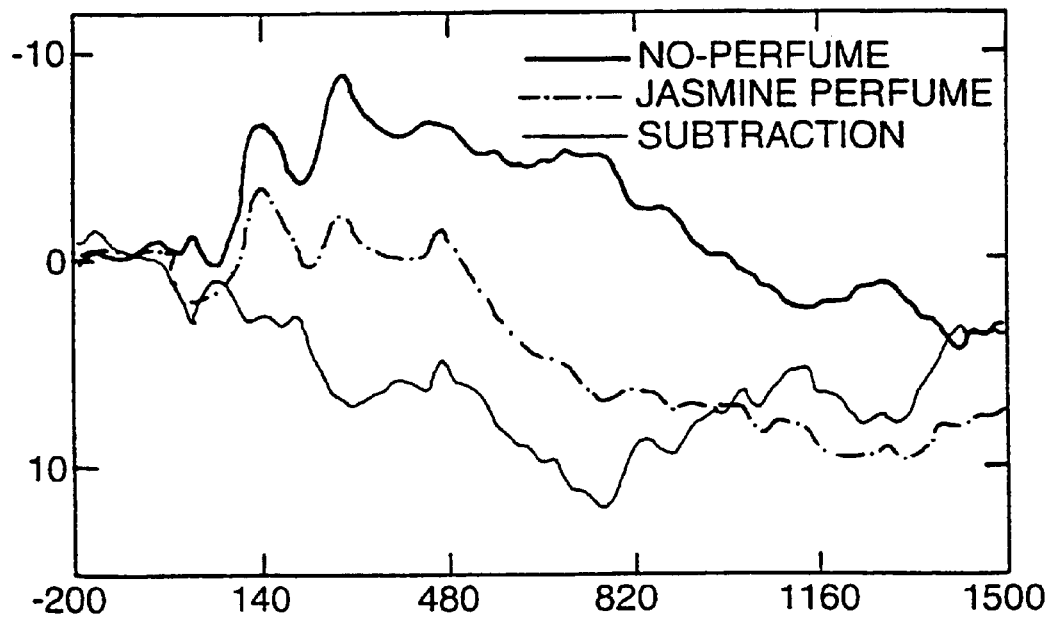
Figure 8C:
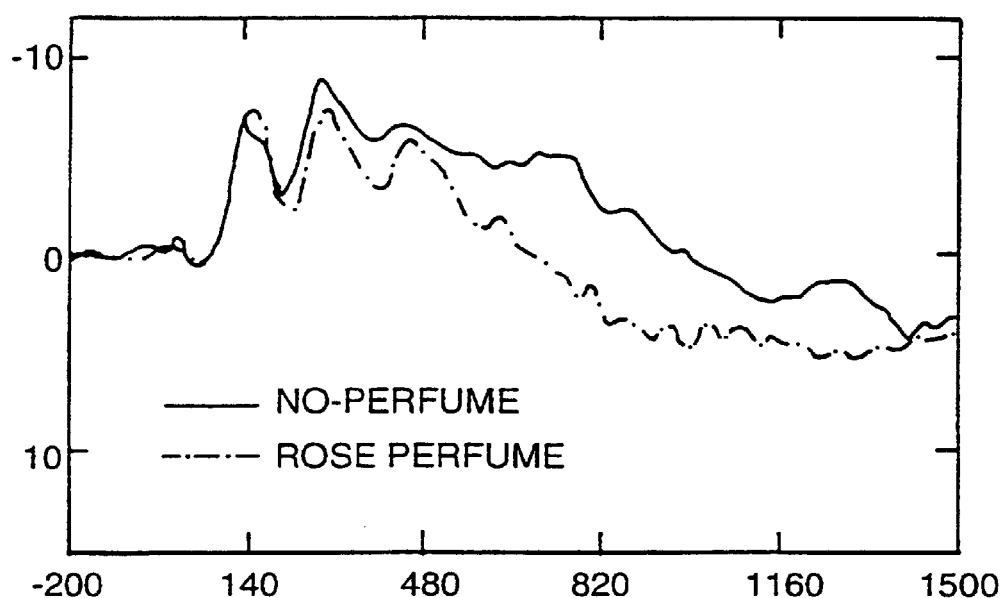
Figure 8D:
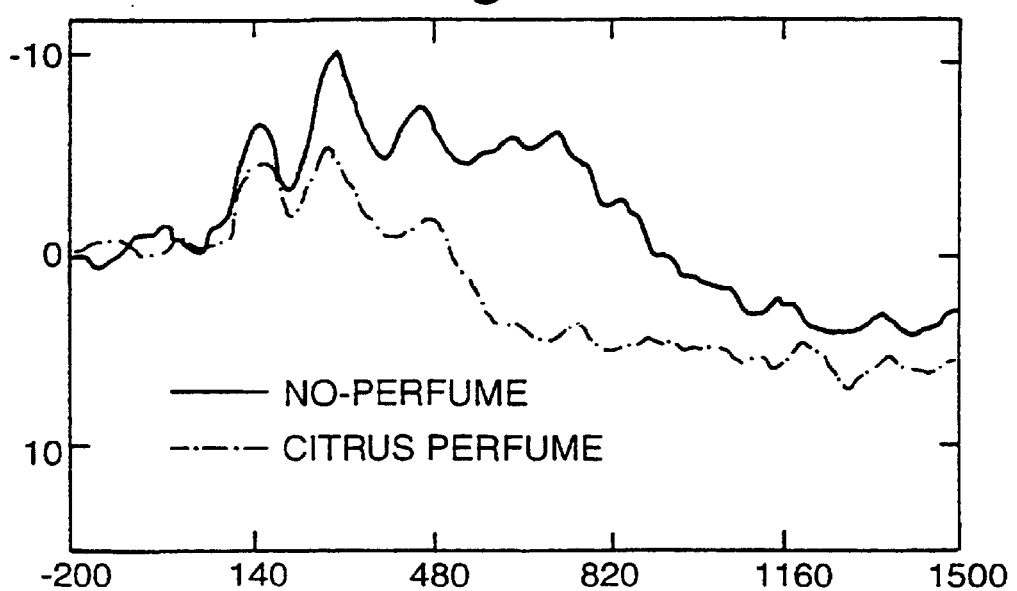
Figure 8E:
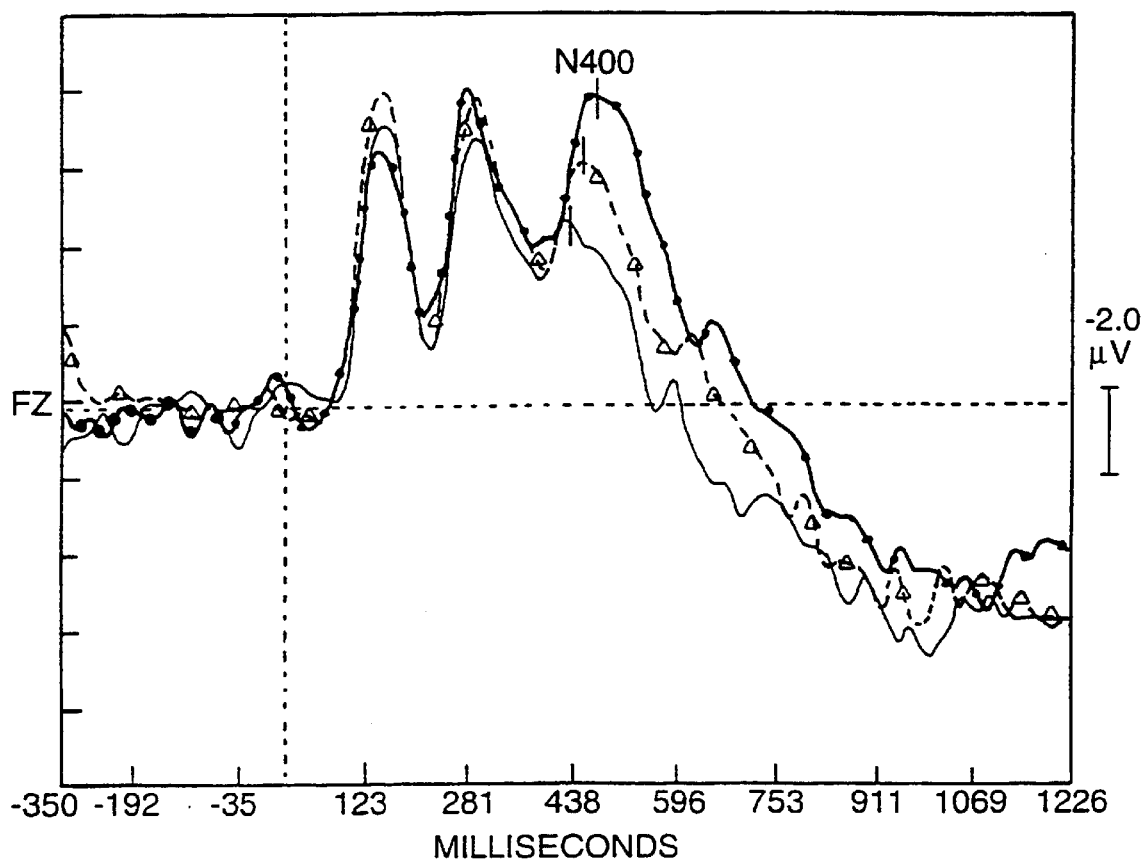

FIG. 5 shows similar ERP traces for averaged results for the Fz electrode (FIG. 5A) and the Pz electrode (FIG. 5B) for fruit pictures, with the dashed lines showing results for no perfume and the other two lines showing results in the presence of fruity (citrus) perfume, either perfume on for 60 seconds (continuous line) or perfume off for 60 seconds (dotted line). These graphs show the ERPs to pictures of fruits while the fruity (citrus) perfume was presented to the subjects elicited more positive-going ERPs. The maximum N400 was obtained frontally and maximum P600 posteriorly. FIG. 6 shows similar ERP traces for averaged results for the Fz electrode (FIG. 6A) and the Pz electrode (FIG. 6B) for non-related pictures, with the dashed lines showing results for no perfume and the other two lines showing results in the presence of floral perfume, either perfume on for 60 seconds (continuous line) or perfume off for 60 seconds (dotted line). These graphs show the ERPs to pictures of non-related subjects while the floral perfume was presented to the subjects elicited more negative-going ERPs. The maximum N400 were obtained frontally and maximum P600 posteriorly.

EXAMPLE 2

Similar experiments to those described in Example 1, but with stages 2 and 3 performed before stage 1, were carried out with different volunteer subjects, and produced generally very similar results. The order of the no odour and odour situations was reversed to confirm that the effects observed were "odour" not "order" effects.

EXAMPLE 3

Similar experiments to those described in Example 1 were carried out with 10 different healthy volunteer subjects (8 male, 2 female), and visual evoked potentials to pictures of flowers, roses, fruit and citrus fruits and non floral/fruit (unrelated) objects were recorded in the absence and presence of three perfumes: rose, jasmine and citrus. The subjects identified fruit and flowers from non-related pictures while perfume was presented through a face mask. In the absence of any odour the amplitude of N400 was measured and found to be the same for fruit and flower pictures. Presence of perfume caused a positive shift of the evoked potential. Evidence was found that N400 was larger when the picture was incongruent with the perfume.

Experimental details were generally as described in Example 1, although in this case the subjects observed pictures from a sequence of 1170 projected onto a screen and pressed one of 2 buttons according to the class of object depicted. Pictures were of two types; i) flowers and fruits and ii) neither flowers nor fruit, ie unrelated objects such as buildings. Flowers and fruit pictures had subclasses which were roses and citrus fruits. The pictures were presented in random order and displayed for 2 seconds with a 2 second pause between when a fixation cross was displayed; thus there were 15 trials per minute. The recording session was broken into 10 or 20 minute epochs as follows:

10 minutes—No perfume. Pictures of roses, other flowers, fruit and unrelated objects.
20 minutes—Rose perfume. Pictures of roses, other flowers, fruit and unrelated objects.
15 minute break for ventilation and relaxation.
20 minutes—Citrus perfume. Pictures of citrus fruit, other fruit, flowers and unrelated objects.
15 minute break.
20 minutes—Jasmine perfume. Pictures of roses, other flowers, citrus fruit, other fruit and unrelated objects.

Figure 7:
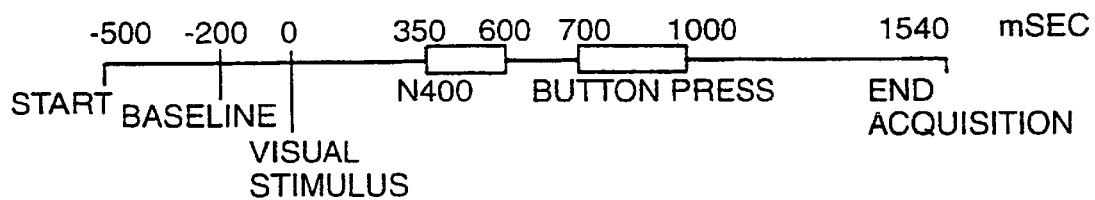
FIG. 7 illustrates schematically the timing of events during each measurement sweep of Example 3.

ERP signals were recorded from 16 electrodes mainly at the locations specified in Example 1, but with electrodes at positions O1 and O2 instead of Fp1 and Fpz. Signals were recorded from 500 msec before the onset of a stimulus until 1540 msec after. Subjects had no difficulty with the task, but the computer recorded their response type. The class of the stimulus was also recorded with each sweep so that each class could be averaged separately and any incorrect responses could be omitted. FIG. 7 indicates the arrangement of each recorded sweep. N400 occurs during the 350–600 msec window after the visual stimulus, and the subjects pressed the button between 700 and 1000 msec. Each sweep lasted 4 seconds.

Perfumes were jasmine, rose and citrus in a diphenolglycolate (DPG) vehicle as prepared by Quest International. After recording, subjects were asked if they could identify the perfumes used from a set of 5 perfumes.

The subjects were instructed to press the left hand button when the picture was fruit or flower and the right hand button for any other object. They were not required to match the object to the odour, nor to distinguish fruit from citrus fruit etc. They were informed that odours would be added from time to time but they were not required to identify the type of odour. Debriefing ensured that they had detected the odours: subjects all identified the rose and jasmine perfume; they were less certain of the citrus perfume.

Each recorded sweep consisted of 16 scalp potentials, an eye movement monitor, and the type of stimulus (flower, fruit or unrelated). Afterwards each sweep was visually inspected for artefact and those with excessive noise, eye blinks or other eye movement and incorrect or absent responses were rejected. The number of incorrect or absent responses amounted to about 1% of the total trials. Accepted signals were averaged according to their object labels and further processing was performed such as smoothing, scaling and measurement of amplitudes and latencies of the waveforms. Fifty sweeps of each object type were available for averaging. Usually not more than 10% had to be rejected because of artefact.

The N400 potential amplitude was analysed; this was defined as the negative peak occurring between 350 and 600 msec after the visual stimulus. The amplitude was taken as the mean of the peak point and 5 samples on each side. That is the mean of 11 points sampled at 4.7 msec per point or the mean amplitude over a 52 msec period. Statistical analysis was by paired t test and repeated measure analysis of variants (ANOVA) implemented by the Statistical Package for Social Sciences (SPSS). Grand averages of evoked potentials are shown in the FIG. 8 but statistics were performed on each subject individually.

Results

Results are illustrated in FIGS. 8 to 11. In these Figures, time is in msec and the baseline was taken as the mean amplitude of the 200 msec preceding the visual stimulus presented at time 0 msec. Negativity is denoted by an upward deflection in $\mu$V.

In FIG. 8 the grand averages of evoked potentials from the Fz scalp location are shown when the subjects viewed a randomly presented series of pictures of flowers and fruits and unrelated objects, in the presence or absence of perfume. FIG. 8a shows evoked potentials to fruit and flower pictures with no perfume present. The solid line shows results for fruit pictures and the dashed line shows results for flower pictures. Both fruit and flowers give almost identical potentials and subtraction of the two traces (the faint line) leaves a difference potential close to zero. There is no statistically significant difference between the N400 evoked potentials of fruits and flowers (see Table 2 below). FIG. 8b shows evoked potentials for flower pictures with no perfume (solid line) and another trace for flower pictures viewed in the present of jasmine perfume (dotted line). The substraction trace (faint line) shows a clear different with a positivity beginning at about 200 msec after the stimulus and lasting over 1 second. FIGS. 8c and 8d are similar examples where flower pictures were viewed in the presence or absence of rose perfume (FIG. 8c, solid line no perfume, dashed line rose perfume) and fruit pictures in the presence or absence of citrus perfume (FIG. 8d, solid line no perfume, dotted line citrus perfume). In both cases, the addition of perfume results in greater positivity.

Table 4 gives the amplitudes and statistical differences of the N400 potentials. Citrus perfume made a significant difference to the N400 evoked by fruit stimuli and jasmine perfume reduced the N400 amplitude of flower pictures. Although rose perfume did not reduce N400 amplitude, FIG. 8c demonstrates that rose perfume produced a more positive potential but this developed after the N400 wave.

TABLE 4

| Picture | No Perfume | Rose | Jasmine | Citrus |
|---|---|---|---|---|
| FRUIT | 11.0 ± 4.7 | 11.6 ± 3.9 | 8.0 ± 3.8 | 6.4 ± 3.5 |
|  |  | $p > 0.05$ | $p > 0.05$ | $P < 0.01$ |
| FLOWERS | 9.1 ± 3.3 | 9.3 ± 2.6 | 4.2 ± 3.2 | 6.8 ± 4.6 |
|  |  | $p > 0.05$ | $p < 0.001$ | $p > 0.05$ |

In Table 2, the mean and standard deviation of amplitude in $\mu V$ (negative sign omitted) of N400 at Fz evoked by flower and fruit pictures is given without perfume and with the 3 perfumes used. The probability figures show the difference between N400 with and without perfume and those in the last row relate to the difference between fruit and flower pictures (paired t test, n=10).

The hypothesis predicts that N400 will be larger if the visual object is incongruent with the perfume. This is clearly demonstrated in FIG. 8e, which shows results where the subjects smelled a rose perfume in the presence of a series of different pictures. The plain line shows results for rose pictures, the line with triangles results for flower pictures and the line with circles results for fruit pictures. The N400 potential evoked by pictures of roses was significantly smaller than that evoked by fruits, with that to flowers (other than roses) in between the two (N400 roses=7.38±3.16 $\mu V$; N400 flowers=9.30±2.65 $\mu V$; N400 fruits=11.69±3.94 $\mu V$). Thus, responses in the presence of fully congruent odour and image (both of roses) could be readily distinguished not only from those in the presence of totally unrelated odour and image (rose odour and fruit image) but also from somewhat related or semi-congruent odour and image (rose odour and non-rose flower image).

Figure 9:
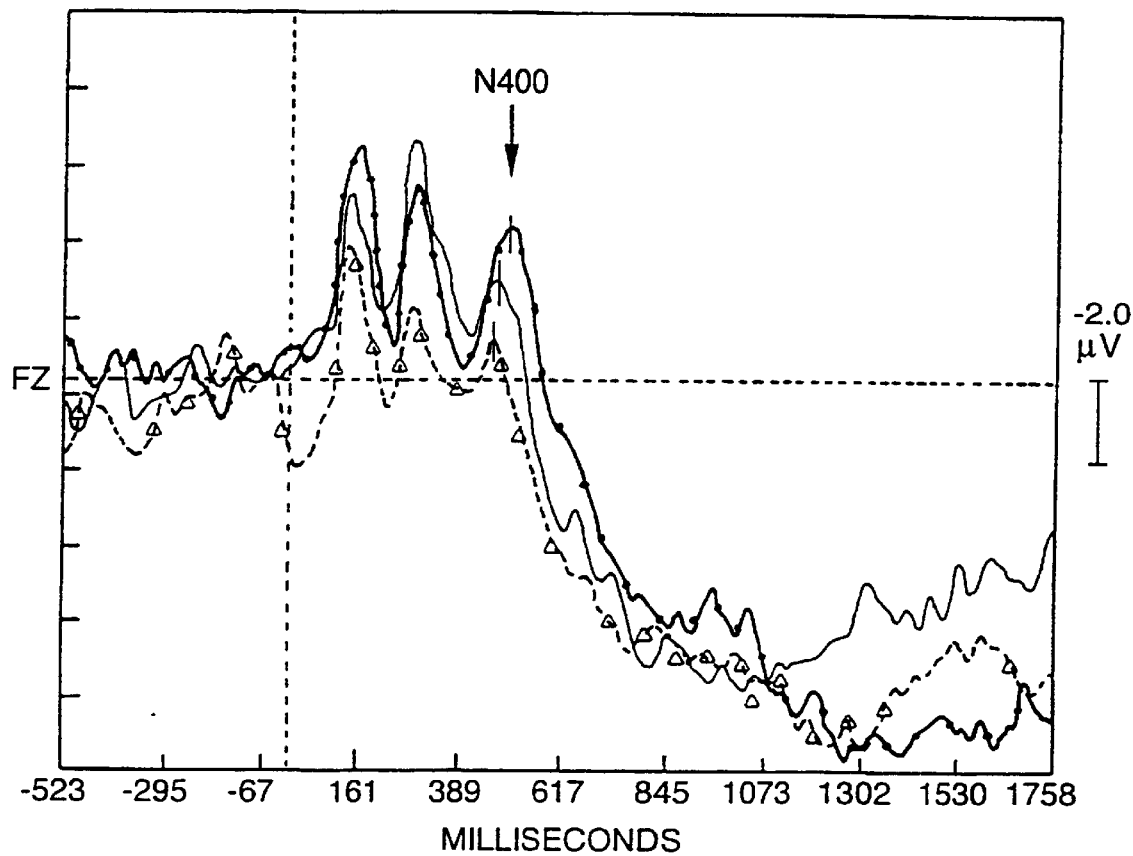
FIGS. 9 to 11 are graphs of potential ($\mu$v) from Fz electrodes versus time (msec), showing further results from Example 3.

FIG. 9 similarly shows results for jasmine perfume with flower pictures (congruent) (line with triangles), rose pictures (semi-congruent) (full line) and citrus pictures (incongruent) (line with circles).

Figure 10:
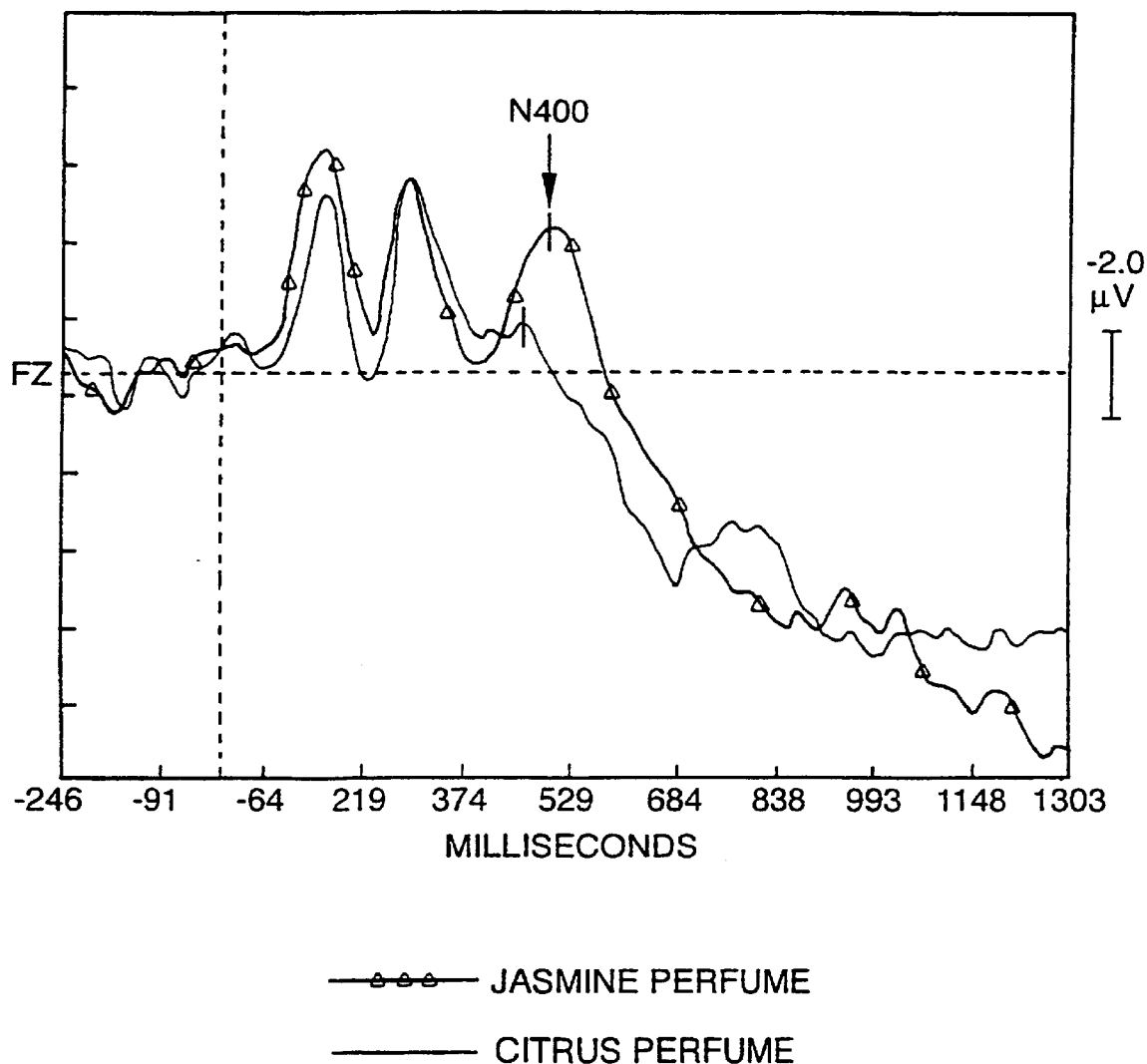

FIG. 10 similarly shows results for citrus pictures with citrus perfume (congruent) (plain line) and jasmine perfume (incongruent) (line with triangles).

Figure 11:
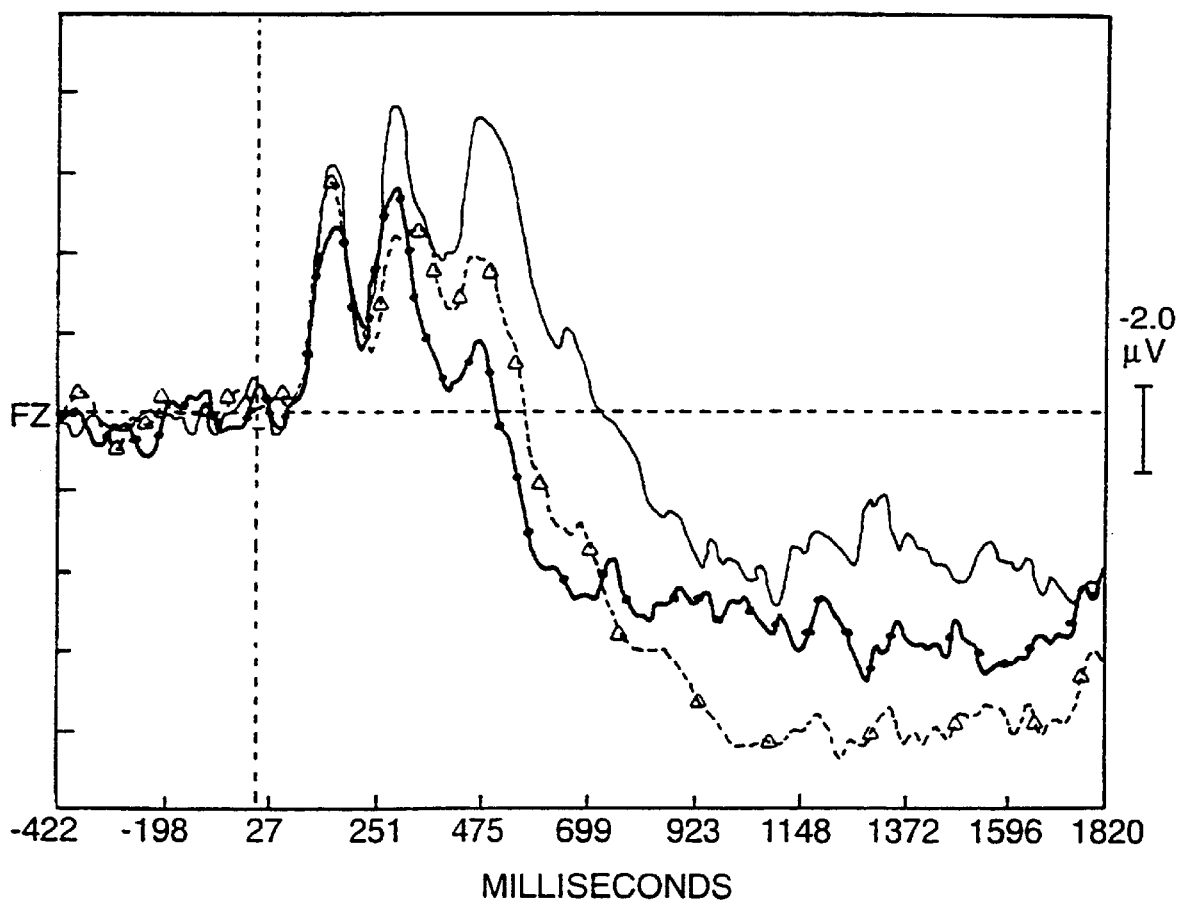

FIG. 11 similarly shows results for fruit pictures with citrus perfume (congruent) (line with circles), jasmine perfume (incongruent/semi-congruent as jasmine has a fruity/floral odour) (line with triangles) and rose perfume (incongruent) (plain line).

Further results (not shown) demonstrate that the presence of any odour reduces the N400 peak, but the degree of the effect is dependent on the fit or congruency of the picture and odour.

The latency of the N400 peak was also measured and the results were categorised according to whether the situation was congruent (eg rose picture with rose perfume) or incongruent (eg rose picture with citrus perfume). Differences in latency between the two treatments were found across the frontal areas of the brain. This was found to be statistically significant on measurements taken from the F3 and Fz electrodes. See results in Table 5.

TABLE 5

Mean Latency measurements (msecs)

|  | Congruent | Incongruent | t-value | Sig |
|---|---|---|---|---|
| F3 | 424.783 | 449.347 | 0.1588 | ns. |
| F4 | 418.058 | 455.540 | 0.0209 | $p \leq 1\%$ |
| Fz | 428.094 | 458.454 | 0.0298 | $p < 1\%$ |

The response time of the subjects taken to press a button after a picture was shown was recorded as shown in Table 6.

TABLE 6

Mean Response time measurements (msecs)

| Picture | Perfume | Response Time | Std. Dev. |
|---|---|---|---|
| Citrus | Citrus | 635.196 | 165.902 |
| Citrus | Jasmine | 636.847 | 133.744 |
| Flowers | Jasmine | 613.488 | 142.166 |
| Flowers | Rose | 626.348 | 142.749 |
| Flowers | Citris | 696.249 | 162.178 |
| Flowers | None | 702.306 | 199.931 |
| Fruit | Citrus | 630.981 | 187.455 |
| Fruit | Jasmine | 642.719 | 144.829 |
| Fruit | Rose | 664.763 | 146.183 |
| Fruit | None | 723.255 | 127.964 |
| Rose | Rose | 623.137 | 119.751 |
|  | Jasmine | 640.666 | 139.063 |

The response times are shorter when the situation is congruent (eg fruit picture with citrus perfume) than when it is incongruent (eg fruit picture with rose perfume). This effect was tested using an Analysis of Variance and found to be significant as shown in Table 7.

TABLE 7

Analysis of variance
Tests of significance for MEAN using SEQUENTIAL sums of squares.

| Source of Variance | SS | DF | MS | F | Sig. of F |
|---|---|---|---|---|---|
| Residual | 233587.27 | 72 | 3244.27 |  |  |
| FName | 2133379.43 | 9 | 237042.16 | 73.06 | .000 |
| FCongruence | 24805.38 | 2 | 12402.69 | 3.82 | .026 |
| FPerfume | 25487.39 | 2 | 12743.69 | 3.93 | .024 |
| FCon + FPerf. | 52918.61 | 4 | 13229.65 | 4.08 | .005 |

EXAMPLE 4

Further experiments were carried in which N400 ERP traces were monitored using a slightly different technique to that of Examples 1, 2 and 3. These further experiments again showed that the N400 deflection is greater if there is no match or congruence between a simultaneously presented odour and picture.

The experiments used an olfactometer with a multi-input nozzle. A Neuroscan Inc 32 Synamps EEG Amplifier (model number 50835/N) (Neuroscan and Synamps are Trade Marks) was used to collect the electrical activity of the cortex. Three Kodak (Kodak is a Trade Mark) slide projector carousels were used to back project images onto a translucent screen. A white noise generator and headphones were used to provide a masking sound. An Apple Macintosh 11SI computer (Apple and Macintosh are Trade Marks) ran a program which synchronised all the equipment used in the study.

The olfactory stimuli used were four synthetic odorants: rose, lemon, grass and leather. The odorants were diluted using dipropylene glycol (DPG) and judged to be isointense by 10 subjects taking part in a pilot study. The rose, lemon and grass solutions were each diluted using equal volumes of DPG. The leather odour was diluted 1/10, ie 1 part leather odour in 10 parts DPG. A total of 75 mls of each odour was prepared and placed in the olfactometer bottles. Each odour was screened in the pilot study by subjects who rated each odour for familiarity, isointensity and for their match to the visual stimuli.

The olfactometer presented each odorant in a stream of charcoal filtered air at room temperature using a flow rate of one litre per minute. Presentations of the odours was for a period of four seconds. The odour streams were delivered just below the subject's nose using a multi-input nozzle. Each odour was delivered to the nozzle via separate lines. During periods when the odours were not being presented a stream of room temperature humidified air was delivered via the multi-input nozzle. The odour deliveries were controlled by the computer.

Each of the odours was represented by photographs. These consisted of 35 standardised and professionally taken coloured slides presented via the three Kodak carousel projectors. Slide presentations were controlled by the computer and were carefully synchronised with the priming odour. Each of the four priming odours was presented with 8 slides. For six of the slides the odour matched the image and for two of the slides the odour did not match the image. For example, an odour-matched image for the smell of grass was a slide showing a picture of grass. The odour-mismatched image was a slide showing an image of a road surface. The mismatch images were selected to be visually similar either in terms of shape or size. The mismatched visual stimuli were:

Grass: Slide 1; Road Surface, Slide 2; Beach

Leather: Slide 1; Stool, Slide 2; Plant

Rose: Slide 1; Baseball Bat, Slide 2: Cricket Bat

Lemon: Slide 1; Rugby Ball, Slide 2: Electrical plug.

In order to reduce boredom and to ensure the subjects watched the viewed pictures each view was taken from a different angle so that no slide was repeated.

The slides were back projected onto a 160×109 cm translucent screen, with each slide being projected at a visual angle of 45°. The slides were projected through a neutral density filter to standardise the overall luminance. The subject was seated 1.5 m in front of the screen with his or her chin placed on a chin rest, adjusted for each subject to be a comfortable fit. Visual stimuli were presented for 800 msec and, as mentioned above, a 80/20 matched/mismatch ratio was used.

The ERPs were recorded using a commercially produced electrode cap and using a Neuroscan Inc, 32 channel Synamps machine, model no. 50835/N. The electrodes were referenced to linked mastoids using a forehead electrode as ground. All impedances when recording were generally below 15 kOhms and more usually below 7 kOhms. The total recording epoch was 1200 ms with a 200 ms pre-stimulus and a post-stimulus period serving as a baseline. Sampling rate was 1200 Hz. The ERP trials were recorded individually and tagged in order to allow for later off-line averaging into matched and mismatched trials.

Following completion of various questionnaires, a cap was fitted to the subject and Omni-prep used to prepare the scalp sites and SLE electrode gel inserted into the individual electrode cups. Electrodes were positioned at the following locations, identified by the internationally recognised placement notation referred to in Example 1: Fpz, Fp1, Fp2, F7, F3,.F4, Fz, F8, F17, FrC1, FC3, FCz, FC4, FTC2, Fr8, T3, C3, Cz, TCp1, Cp3, Cpz, Cp4, TCp2, T5, P3, Pz, P4, T6, Tp7, PO1, PO2, Tp8, O1, Oz, O2 A1 (left ear) and A2 (right ear). The multi-input nozzle from the olfactometer was then adjusted to a position just below and in front of the nose of the subject. Headphones were carefully placed over the subject's ears, to ensure no changes in electrode positions or impedances. The white noise generator was switched on and the volume adjusted to a level comfortable for the subject but one which would mask any sounds from the apparatus. This was achieved by checking with the subject that the sound of the olfactometer switches were masked. The experimenter was able to communication with the subject via headphones. Attempts were made to reduce any anxiety of the subjects who were, during the experimental phase, sat in a darkened environment surrounded by apparatus. Subjects then read the following instructions and encouraged to ask any questions they might have.

Instructions to Subjects

"This experiment relies upon your breathing technique. You are required to breathe in through your nose and out through your mouth. The brass nozzle in front of your nose may or may not deliver an odour. Please breathe through your nose evenly and there is no need to sniff. Try to remain as relaxed as possible throughout the experiment. A light will appear in order to alert you to the presentation of an odour. At this time place your chin in the chin rest and begin breathing in through your nose and out through your mouth and try not to move your head from side to side. Following the odour a second light will appear to alert you to the presentation of a slide on the screen in front of you, showing a colour slide which will either be related to the odour you have just received or bear no relation to the odour. You are not required to make an oral verbal judgement during the experiment but simply make conscious decisions as to the relationship between the two stimuli. It does not matter if you recognise the odour but are unable to name it, simply concentrate on deciding if the two stimuli are related. Please try not to blink, swallow or make any motor movement following the second light until about 1 second after the slide has been switched off. Please ignore the video camera which is recording your eye movements and try to keep you eyes focused on the centre of the screen. The headphones you are wearing will produce white noise in order to reduce the sounds of the various pieces of equipment used to run the experiment. Three practice trials will be given, followed by a break. Please ask any questions or make any comments you feel are relevant. This will then be followed by 32 experimental trials. Do you have any questions or require further information before you begin? Thank you for participating".

Subjects were instructed about the breathing technique required and then given the three warm-up practice trials. The method of breathing required was in order to prevent retronasal stimulation of the olfactory receptors. Once this phase had been satisfactorily completed the illumination level in the room was lowered and the computer program and the ERP recordings started. During the 32 experimental trials an orange warning light was illuminated for 1 second in order to alert subjects to the impending odour and the need for the required breathing pattern. An odour was presented for 4 seconds. A red light was illuminated to warn the subject about the impending slide presentation. Slide presentation lasted for 0.8 seconds. The warning lights enabled subjects to reduce muscular movements during the presentation of stimuli. Subjects were asked to look at a fixation point on the screen. To help them do this a dot was present at all times, other than during the actual slide presentations, in the centre of the screen. Following slide presentation, subjects were required to make a subvert decision about the relationship, if any, between the odour and the slide. However, no oral or motor response was required during the experimental trials.

The EEG recordings were started 0.2 seconds before the projection of the slide and lasted until 0.2 seconds post picture offset. The slides were projected for a total period of 0.8 seconds. EEG recordings thus lasted for 1.2 seconds. An intertrial interval of 40 secs was used between each of the 32 trials. After all the experimental trials had been completed subjects were again presented with the same 32 stimuli in a similar order and asked say if the odour matched the slide. This was carried out in order to confirm that subjects had performed the task correctly. 21 healthy volunteer subjects (11 males and 10 females) were tested in this way, and results were as follows.

Data Treatment

Off-line editing of post recording data included digital filtering at 0.03 and 30Hz (24bd/oct). Baseline offset alignment, artificial rejection of trials containing in excess of 75 microvolts. Trials containing eye movements were corrected using a standard algorithm. Analysis was initially performed on a subject by subject basis on the Neruoscan Synamps by selecting the matched and mismatched ERP trials for each subject for each electrode site. This data was printed as two grand average wave forms (match and mismatch for each electrode for each subject). The original ASCII raw data was then imported into SPSS. The statistical analysis was performed on an Apple Macintosh computer using SPSS statistical package version 6.1.

Results

A latency window was selected based on the hypothesis that the N400 component would be differentially affected by the matched or mismatched conditions. The window selected for the ERP component analysis was between 300–600 ms post stimulus onset or 500–800 ms from the start of the recording. The minimum amplitude values were selected from the 300 data points within this latency window and subjected to an SPSS repeated measures ANOVA with the factors being sex×electrode×condition. All significant results quoted are at least significant to $p<0.05$. All reported Anova results are quoted using Greenhouse-Geisser tests for significance.

Figure 12:
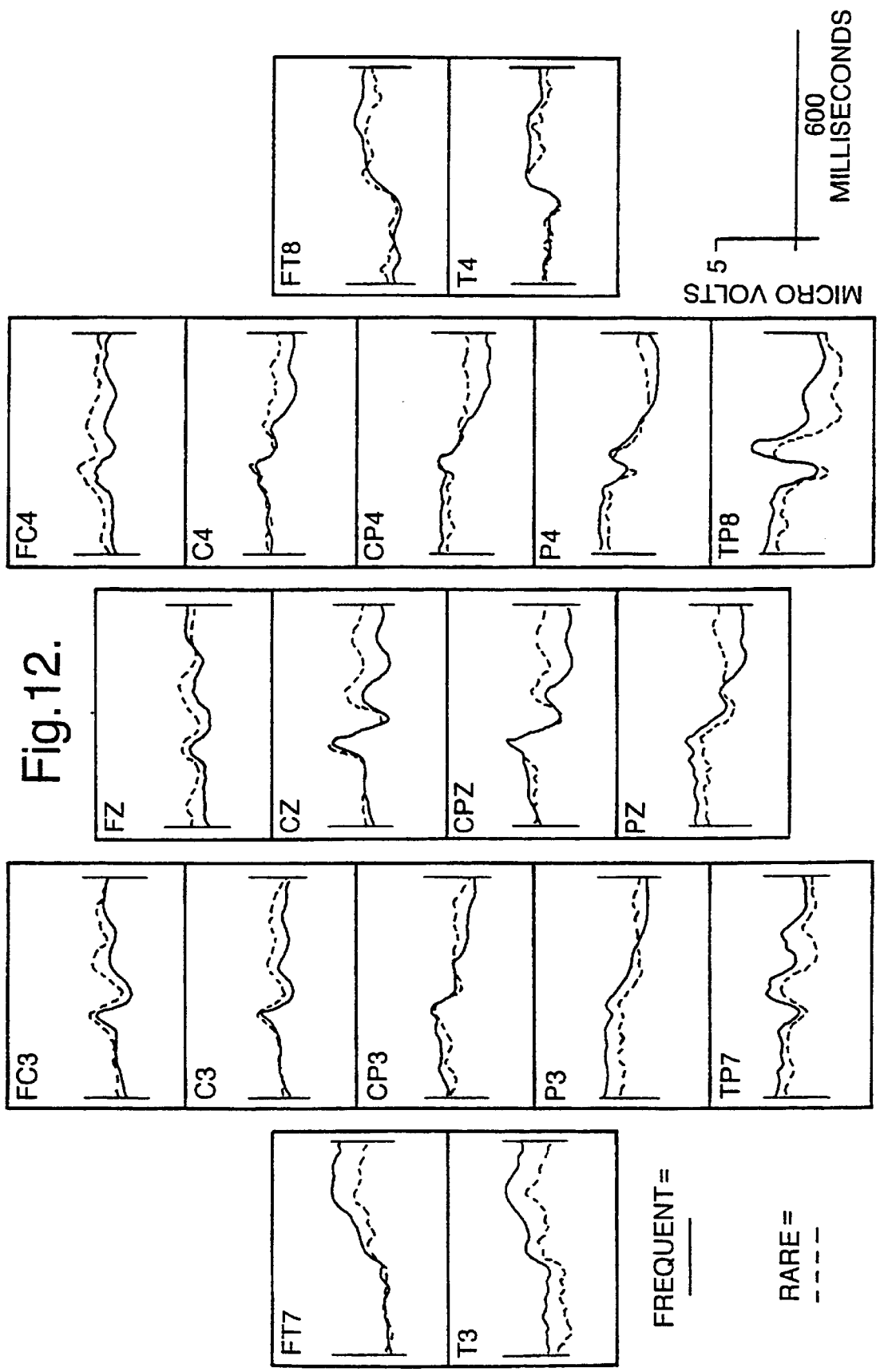
FIG. 12 is a series of graphs of potential versus time, showing grand mean waveforms for 18 selected electrodes monitored in Example 4.

The wave forms of the subjects suitable for analysis were visually inspected and, in order, to reduce the data to manageable proportions 18 electrode sites were selected and used for the quantitative analysis. The selected electrodes were Fz, FT7, FT8, FC3, FC4, Cz, C3, C4, Cp3, CP4, Cpz, T3, T4, Tp7, Tp8, Pz, P3 and P4. Traces showing the wave forms of the grand averages for each of the electrodes are shown in FIG. 12. The electrodes are grouped into midline, left and right hemispheres. The electrode grand means for the matched (frequent) and mismatched (rare) condition of the 18 electrodes are shown in FIG. 13. At all sites the rare value is more negative than the frequent value.

Overall there was a significant condition effect (F, 15.63; df 20,1; p.001) for the N400 wave form showing a significant difference for the 21 subject used in this study between the matched and the mismatched conditions.

Female subjects showed an overall significant condition effect (F, 8.45; df, 1/10; p.016). This was also shown to be the case for males subjects but it was more marginal (F,5.59; df,9/1; p.042). Males and females showed no significant hemispheric or electrode effects and no significant interactions.

The results show conclusively that there is a different in the ERP trace for the N400 waveform when a visual image does not match an odour that was used as a prime. A negative peak with a latency of around 400 msec post stimulus onset was produced for both matched and mismatched stimuli but the later peak was statistically significantly greater. No overall hemispheric effects were obtained and Amplitude differences were greatest over the midline electrodes Fz, Cz, Cpz and Pz.

EXAMPLE 5

The technique employed in Example 1 was used to test various odours for congruence or otherwise to a series for presented images, and the results used as a basis of odour selection for a particular purpose, eg for use in a fragrance in a particular product. By selecting the odours having an decreased negative ERP response in the 200 to 600 msec post stimulus response (N400), those most congruent to a target image can be selected.

What is claimed is:

1. A method of odour selection for selecting an odour to match a visual or auditory target stimulus, comprising evaluating a number of odour/target stimulus combinations by testing a subject by presenting the subject with one or more odours under different conditions, at least some conditions being in the presence of one or more visual or auditory target stimuli monitoring brain activity of the subject and evaluating the monitored brain activity in relation to odour/target stimulus combinations presented to the subject and selecting the odour/target stimulus combination or combinations indicated as having the greatest degree of association.

2. A method according to claim 1, wherein the target stimulus comprises one or more photographs, drawings or other still images, a film or video sequence, or one or more objects.

3. A method according to claim 1, wherein the target stimulus comprises spoken words, a musical phrase or sequence, a sound effect, a conversation, animal sounds.

4. A method according to claim 1, wherein the odour or odours under test comprise one or more fragrances, fragrance components or fragranced products.

5. A method according to claim 1, wherein a plurality of different subjects are tested, and the results of the tests analyzed and combined to give overall test results.

6. A method according to claim 1, wherein electrical activity of the brain is monitored.

7. A method according to claim 6, wherein event related potentials of the brain are monitored by electroencephalography.

8. A method according to claim 7, wherein the negative peak occurring between 350 and 600 msec after presentation of the visual or auditory target stimulus (N400 potential) is monitored.

9. A method according to claim 6, wherein scalp midline electrical activity is monitored.

10. A method according to claim 1 wherein the subject is required to react to presentation of a visual or auditory target stimulus, and response time is measured.

11. A method according to claim 1, wherein the subject is not required to consider the relationship between odour/target stimulus combinations during testing.

12. A method according to claim 1 wherein the odour is a fragrance intended to be used to perfume a product and the visual or auditory target stimulus is or represents the product or a desired attribute of the product.

* * * * *